United States Patent
Worrell et al.

(10) Patent No.: US 10,813,684 B2
(45) Date of Patent: Oct. 27, 2020

(54) CONTROL OF CUTTING AND SEALING BASED ON TISSUE MAPPED BY SEGMENTED ELECTRODE

(71) Applicant: Ethicon Endo-Surgery, LLC, Guaynabo, PR (US)

(72) Inventors: Barry C. Worrell, Centerville, OH (US); David James Cagle, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 639 days.

(21) Appl. No.: 14/673,155

(22) Filed: Mar. 30, 2015

(65) Prior Publication Data

US 2016/0287316 A1    Oct. 6, 2016

(51) Int. Cl.
*A61B 18/14* (2006.01)
*A61B 18/00* (2006.01)

(52) U.S. Cl.
CPC ...... *A61B 18/1445* (2013.01); *A61B 18/1482* (2013.01); *A61B 2018/0063* (2013.01); *A61B 2018/00601* (2013.01); *A61B 2018/00755* (2013.01); *A61B 2018/1455* (2013.01)

(58) Field of Classification Search
CPC .......................... A61B 18/1442; A61B 18/1445
See application file for complete search history.

(56) References Cited

U.S. PATENT DOCUMENTS

| | | | | |
|---|---|---|---|---|
| 6,217,574 B1 * | 4/2001 | Webster | ............. | A61B 18/1492 606/34 |
| 8,298,232 B2 | 10/2012 | Unger | | |
| 2002/0026127 A1 * | 2/2002 | Balbierz | ............ | A61B 18/1206 600/567 |
| 2010/0331838 A1 * | 12/2010 | Ibrahim | ................. | A61B 17/28 606/52 |
| 2012/0083783 A1 * | 4/2012 | Davison | ............. | A61B 18/1445 606/45 |
| 2012/0083835 A1 * | 4/2012 | Shelton, IV | ...... | A61B 17/00491 606/219 |
| 2012/0116379 A1 * | 5/2012 | Yates | ............... | A61B 17/00234 606/33 |
| 2013/0103035 A1 * | 4/2013 | Horner | ............... | A61B 18/1445 606/51 |
| 2013/0161374 A1 * | 6/2013 | Swayze | ................ | A61B 17/068 227/176.1 |
| 2013/0253508 A1 * | 9/2013 | Ide | ........................ | A61B 18/085 606/41 |
| 2013/0296840 A1 * | 11/2013 | Condie | .................. | A61B 90/06 606/33 |

* cited by examiner

*Primary Examiner* — Michael F Peffley
*Assistant Examiner* — Bo Ouyang
(74) *Attorney, Agent, or Firm* — Mintz Levin Cohn Ferris Glovsky and Popeo, P.C.

(57) ABSTRACT

Devices and methods for sealing and cutting tissue are provided in one exemplary embodiment, the device includes a proximal handle portion, an elongate shaft, and a jaw assembly having first and second jaws. At least one of the jaws includes an electrode that is segmented into a plurality of zones. Each zone includes a parameter monitor, and the parameter monitors provide information about the tissue that is then mapped to define one or more characteristics of the tissue. A controller can then be operated to adjust functionality of the device within each zone based on the mapped parameters/characteristics. Other devices and methods for sealing and cutting tissue are also provided.

20 Claims, 9 Drawing Sheets

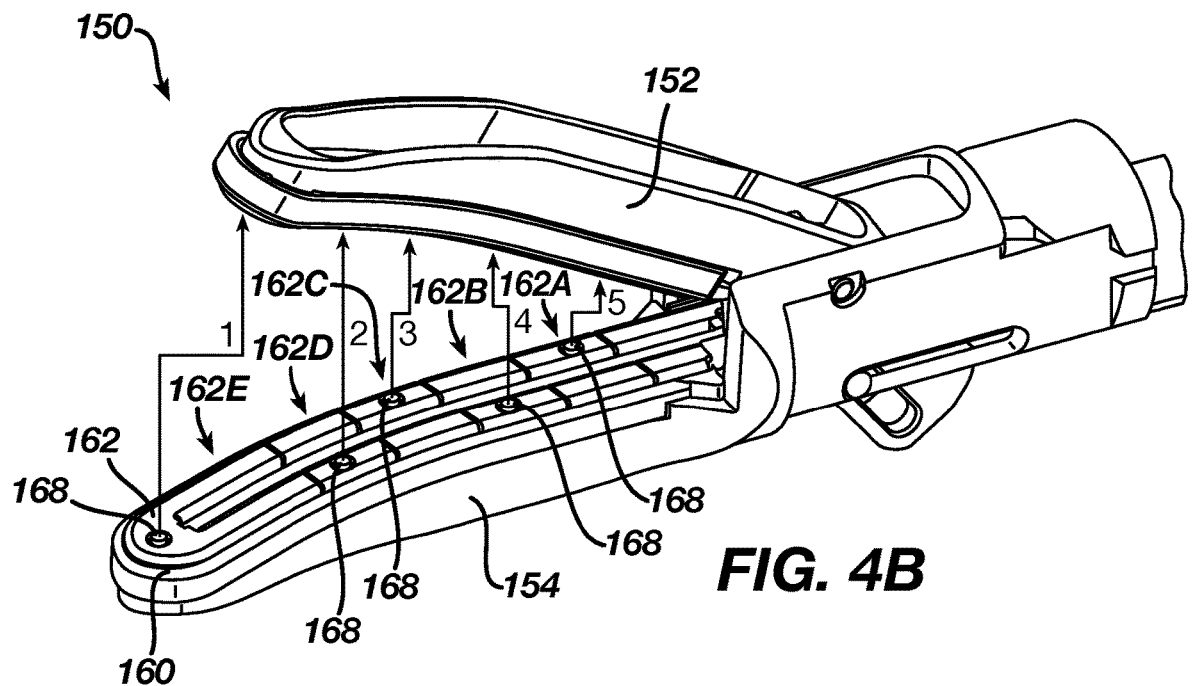
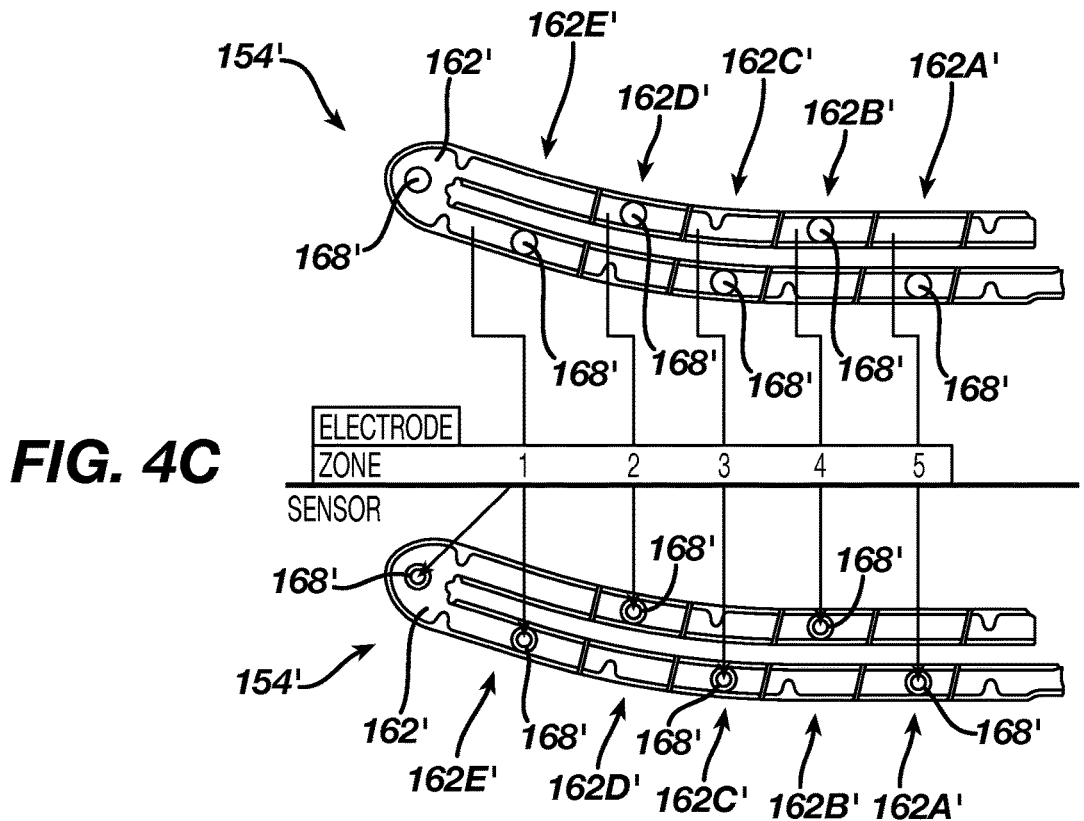

CONTROL OF CUTTING AND SEALING BASED ON TISSUE MAPPED BY SEGMENTED ELECTRODE

FIELD

The present invention relates to surgical devices and methods for sealing and transecting tissue, and more particularly to improved devices and methods for controlling a cutting blade and/or the application of energy through various zones of an end effector.

BACKGROUND

Surgical devices are used in various open, endoscopic, and laparoscopic surgeries to seal and transect tissue volumes and blood vessels. The devices generally include jaws for grasping tissue therebetween and a cutting mechanism that is advanced through the grasped tissue to transect it. In some instances the devices are configured to apply electrical energy to the grasped tissue to seal it before tissue transection is completed. For example, various mono-polar and hi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

One issue that can plague devices of the nature described above is that it can be difficult to work with tissue of varying thickness or different tissue types grasped across an elongate length of the jaws. A cutting blade can jam as it tries to pass through the jaws to transect the tissue, or a seal may not take because the amount of energy applied to the tissue is not appropriate for the thickness of tissue disposed between the jaws.

It would be desirable for systems, devices, and methods to be created that allow a user to better negotiate and manage device performance based on the type of tissue and thickness of tissue disposed across a length of an end effector of that system or device, thereby affording a surgeon more control during the course of the procedure.

SUMMARY

Devices and methods are generally provided for sealing and cutting volumes of tissue and blood vessels. In one exemplary embodiment, a surgical device includes a proximal handle portion having a driver, an elongate shaft extending distally from the handle portion, a jaw assembly, a cutting blade, and a controller. The jaw assembly has a first jaw and a second jaw pivotally coupled thereto, with the first jaw having a tissue-engaging surface that is opposed to a tissue-engaging surface of the second jaw. At least one of the tissue-engaging surfaces of the first and second jaws includes an electrode segmented into a plurality of zones, with each zone being configured to apply energy supplied by power from the driver to tissue disposed between the first and second jaws to seal the tissue. Further, each zone has a parameter monitor disposed therein, with the parameter monitor being configured to measure a parameter that is commensurate to a thickness of tissue disposed between the first and second jaws. The cutting blade has a distal portion disposed between the opposed tissue-engaging surfaces of the first and second jaws, with the distal portion including a terminal, vertically disposed cutting edge that extends vertically between the first and second jaws. The cutting blade translates distally and proximally through the first and second jaws in response to power supplied by the driver. The controller is configured to control power output by the driver to adjust at least one of a speed of the cutting blade translating through the first and second jaws and an amount of energy applied by one or more zones of the plurality of zones of the electrode in response to the parameter measured by the parameter monitor.

In some embodiments, each parameter monitor is configured to measure tissue impedance. Each parameter monitor can include a metal protrusion that extends vertically away from the electrode of the tissue-engaging surface, towards the tissue-engaging surface of the opposed jaw, and each metal protrusion is electrically isolated with respect to the other protrusions. Each metal protrusion can be configured to send a pulse to the opposed jaw to measure tissue impedance at the zone in which the protrusion is located. The electrode can be configured to be selectively switched from being part of a current path extending between the first and second jaws when the jaws are in a closed position, to being isolated from current power supplied by the driver. Further, the device can be configured such that the electrode is switched off prior to measuring impedance at each metal protrusion. The plurality of zones provided for the segmented electrodes can be at least three in some embodiments.

The distal portion of the cutting blade can have an I-beam configuration. For example, the distal portion of the cutting blade can include a first rib extending substantially perpendicular to the terminal, vertically disposed cutting edge and disposed in a track formed in a surface of the first jaw that is opposed to the tissue-engaging surface of the first jaw. Likewise, the distal portion of the cutting blade can include a second rib extending substantially perpendicular to the terminal, vertically disposed cutting edge, substantially opposed to the first rib, and disposed in a track formed in a surface of the second jaw that is opposed to the tissue-engaging surface of the second jaw.

In another exemplary embodiment of a surgical device, the device includes a proximal handle portion having a motor disposed therein, an elongate shaft extending distally from the handle portion, a lower jaw, an upper jaw, a cutting blade, a plurality of metal stand-offs, and a controller. The lower jaw is coupled to a distal end of the elongate shaft, has a tissue-engaging surface that includes an electrode segmented into a plurality of zones, and a channel formed in a surface that is opposed to the tissue-engaging surface. The upper jaw is pivotally coupled to the lower jaw, has a tissue-engaging surface that is opposed to the tissue-engaging surface of the lower jaw such that the two tissue-engaging surfaces are configured to grasp tissue therebetween, and a channel formed in a surface that is opposed to the tissue-engaging surface of the upper jaw. The cutting blade has an upper portion disposed in the channel of the upper jaw, a lower portion disposed in the channel of the lower jaw, and a cutting edge disposed vertically between the upper and lower portions. The upper and lower portions are configured to contact the respective surfaces of the jaws and translate through the channel formed in the respective surfaces in response to power supplied by the motor. The plurality of metal stand-offs are at least one metal stand-off extending vertically from each zone of the electrode of the lower jaw, towards the upper jaw, with each metal stand-off being configured to prevent the electrode of the lower jaw from contacting the tissue-engaging surface of the upper jaw. Further, each metal stand-off is configured to sense impedance of tissue in contact with the respective stand-off.

The controller is configured to adjust a speed of the cutting blade based on the sensed impedance in real time.

In some embodiments each metal stand-off is electrically isolated with respect to the other metal stand-offs. Each metal stand-off can be configured to send a pulse to the upper jaw to measure tissue impedance at the zone in which the metal stand-off is located. The plurality of zones of the segmented electrode of the lower jaw can be at least three, and there can be at least three metal stand-offs, at least one in each zone.

The electrode can be configured to be selectively switched from being part of a current path extending between the lower and upper jaws when the jaws are in a closed position, to being isolated from current power supplied by the motor. The device can be configured such that the electrode is switched off prior to measuring impedance at each metal stand-off. In some embodiments, the tissue-engaging surface of the upper jaw can include an electrode that is opposed to the electrode of the lower jaw.

One exemplary surgical method includes closing opposed jaws of a surgical device on tissue disposed between the jaws, with at least one of the jaws having an electrode disposed on a tissue-engaging surface of the jaw. The electrode is segmented into a plurality of zones, and a cutting blade is disposed between the jaws and configured to translate through at least a portion of the jaws to transect tissue disposed between the jaws. The method further includes measuring a tissue impedance at each zone of the plurality of zones, and operating the surgical device such that a controller of the surgical device adjusts at least one of a speed of the cutting blade as it translates through the first and second jaws and an amount of energy applied by one or more of the zones to the tissue disposed between the jaws based on the tissue impedance measured at the zones.

In some embodiments, the electrode can be disposed on a bottom jaw of the opposed jaws, and the method can further include switching the electrode between a configuration in which it is part of the current path that extends from the bottom jaw to the top jaw, and a configuration in which the electrode is isolated from current power supplied by a driver that powers the cutting blade. In some other embodiments, the electrode can be disposed on a bottom jaw of the opposed jaws, and the method can include turning off the electrode prior to measuring a tissue impedance at each zone of the plurality of zones. The method can further include mapping tissue thickness at each zone based on the measured tissue impedance at each zone. The method can also include detecting tissue type at each zone based on the measured tissue impedance at each zone.

The surgical method can also include applying energy to one or more of the one or more zones based on the tissue impedance measured at the zones. Tissue impedance for one or more of the zones in which energy was applied can then be measured and compared to a threshold impedance value for each zone in which tissue impedance was measured. The applying energy step to a zone of the one or more zones can be repeated until the value of the measured tissue impedance for that zone is equal to or greater than the threshold impedance value for that zone.

BRIEF DESCRIPTION OF DRAWINGS

This invention will be more fully understood from the following detailed description taken in conjunction with the accompanying drawings, in which:

FIG. 4B is a schematic perspective view of the end effector of FIG. 4A, illustrating a pathway from the stand-offs to the upper jaw;

FIG. 4C is a schematic top view of a lower jaw of an end effector of the nature of FIG. 4A, the lower jaw having an electrode associated therewith, the electrode having fives zones formed therein, and at least one sensor being disposed in each zone, the sensors being illustratively mapped to the respective zones;

DETAILED DESCRIPTION

Figure 1:
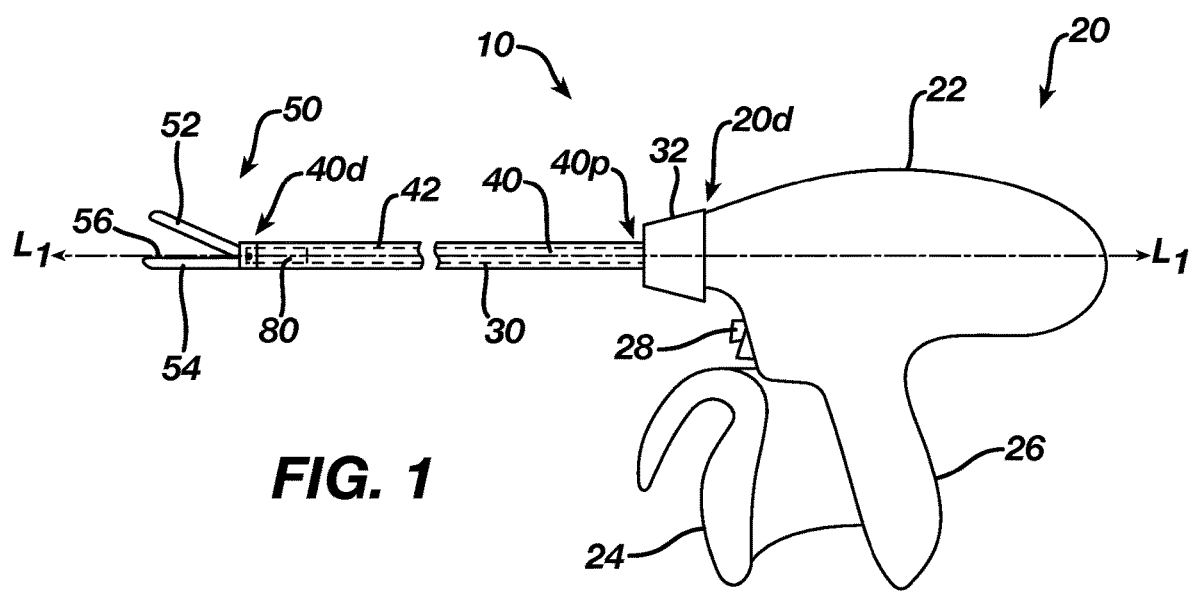
FIG. 1 is side view of one exemplary embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose. Additionally, the pictures are not necessarily to scale. For example, an illustration of a compression member in FIG. 3 is not drawn in the same scale as the end effectors of FIGS. 2A-2C even though the compression member can be disposed in and travel through portions of the end effectors.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Still further, a person skilled in the art will recognize that a number of different terms can be used interchangeably while still being understood by the skilled person. By way of non-limiting example, the terms "cut" and "transect" are generally used interchangeably herein.

The present disclosure generally relates to creating or mapping a more specific profile of tissue disposed in a jaw assembly of a surgical instrument and using that profile to adjust treatments applied to the tissue. The jaw assembly, and more specifically one or more electrodes associated with one or both jaws of the jaw assembly, can define various zones of the jaw assembly, and a parameter associated with the tissue can be measured within each zone. In one exemplary embodiment, the parameter is impedance, which often correlates to a thickness of the tissue, the thickness being a characteristic of the tissue. The measured parameter, or the corresponding characteristic, is then mapped across a length of the jaw assembly. A controller that is either part of the surgical instrument, or electrically coupled thereto, can then modify various functions of the surgical instrument based on the mapped parameter and/or the mapped characteristic of the tissue associated with the mapped parameter. For example, a speed of a cutting blade can be modified based on the thickness of the tissue it is cutting, with a speed generally being slowed down for higher impedance values, and thus thicker tissue. By way of further example, an intensity and duration of energy supplied by an electrode to tissue disposed in the jaw assembly can be adjusted based on the thickness of the tissue, or not even applied if there is no tissue disposed in a particular zone. The ability to better tailor and localize treatments such as cutting and sealing leads to faster, safer, and more efficient treatments.

Surgical Access Device

FIG. 1 illustrates one embodiment of a surgical access device 10 configured to grasp, seal, and transect tissue. The surgical device can include a proximal handle portion 20, a shaft 40, and an end effector 50 for grasping tissue. The handle portion 20 can be designed to operate various features of the end effector 50. For example, the handle portion can close and open a jaw assembly of the end effector 50 to grasp tissue. The jaw assembly can include jaws 52, 54 that are configured to pivot with respect to each other to grasp tissue disposed therebetween. By way of further non-limiting example, the handle portion 20 can initiate the supply of electrical energy to one or more electrodes 56 associated with either or both of the jaws 52, 54 to weld or otherwise seal portions of the grasped tissue. The components to initiate these actions can be part of the handle portion 20 and can extend through or be electrically or mechanically coupled to components that extend through the shaft 40. Components of this nature are known to those skilled in the art, and thus further elaboration related to the same is unnecessary. Further, the handle portion 20 can also be configured to operate other components that work in conjunction with the end effector 50, such as a compression member 80 that can be configured to both move the jaws 52, 54 from an open to a closed position, and to cut tissue grasped by the jaws 52, 54.

Handle Portion

The handle portion 20 can have any type of design known in the art for operating end effectors 50. In the illustrated embodiment, the handle portion 20 has a pistol-grip configuration that includes a housing 22, an actuating handle 24, and a stationary handle 26. Movement of the actuating handle 24 towards the stationary handle 26 can be effective to perform a variety of functions. In the illustrated embodiment, the actuating handle 24 is effective to advance the compression member 80 distally to both close the jaws 52, 54 and cut tissue disposed between the jaws. In some embodiments, the actuating handle 24 can move through two separate cycles or strokes to perform these functions. For example, the actuating handle 24 can move through a first cycle or stroke in which it first moves towards the stationary handle 26 and then returns back to its initial position, during which time its movement towards the stationary handle 26 is effective to close the jaws 52, 54. The actuating handle 24 can then move through a second cycle or stroke, again moving towards the stationary handle 26 and then returning back to its initial position, during which times its movement towards the stationary handle 26 is effective to pass the compression member 80 through at least a portion of the jaws 52, 54 to cut tissue disposed therebetween. As the actuating handle 24 returns to the initial position during the second stroke, the compression member 80 can retract proximally with respect to the jaws 52, 54. In some embodiments, during the second return stroke the compression member 80 can retract to its initial position so that the jaws 52, 54 open, while in other embodiments a separate actuation can be performed to fully retract the compression member 80 to its initial position to open the jaws 52, 54.

The mechanical and electrical components associating the actuating handle 24 with the 54 and or the compression member 80 can be disposed in the housing 22 and the shaft 40, including drivers, controllers, and levers, among other components. For example, the driver can be a motor, such as a pneumatic motor, a hydraulic motor, and/or a solenoid, provided in the handle portion and used to power the compression member, the electrodes, and/or a controller associated with mapping parameters associated with the grasped tissue and adapting functionality of the instrument based on the mapped parameters, as described in greater detail below. Other designs that can be used to actuate the jaws 52, 54 and the compression member 80 include but are not limited to actuator levers, triggers, and sliders. Further, a person skilled in the art will recognize other functions that the actuating handle 24, or other means of actuation, can perform without departing from the spirit of the present disclosure.

The illustrated embodiment also includes an actuator, e.g. a button 28, as part of the handle portion 20. The button 28 can be configured such that pressing it completes a circuit to power the electrode(s) 56, for instance by way of the driver, to seal tissue disposed in the jaws 52, 54. More particularly, completion of the circuit by the button 28 allows electrical energy to pass from a power source (e.g., the driver) disposed in the housing 22, through one or more electrical leads 30, and to the electrode 56. The electrical lead can be disposed in the shaft 40 to electrically connect the button 28 and the electrode 56. Although the power source is described as being in the housing 22, in other embodiments the power source can be external of the housing 22 and the housing can be configured to electrically connect to the power source, for instance by way of a socket extending from the housing 22 to connect to the power source. Similar to the actuating handle 24, a person skilled in the art will recognize that the actuator can have a variety of other designs, and can perform a variety of other types of functions, without departing from the spirit of the present disclosure.

Other features to assist in moving and actuating the components of the device 10 can also be incorporated into the handle portion 20. By way of example, the handle portion 20 can include a rotatable knob 32 disposed at a distal end 20d of the handle portion 20 to facilitate rotation of the shaft 40, and thus the end effector 50 coupled thereto, with respect to the handle portion 20 around a centrally disposed longitudinal axis $L_1$ of the shaft 40. A person skilled in the art will recognize other non-limiting examples of features that can be incorporated with the handle portion 20 to assist in manipulating or otherwise operating the device include: (1) an actuation or articulation lever for articulating the end effector 50; (2) a retraction handle for retracting the compression member 80 towards and/or to its initial position in place of or independent of any retraction that is part of a firing stroke initiated by the actuating handle 24; (3) a firing lockout assembly to prevent the compression member 80 from being actuated at an undesirable time; and (4) an emergency return button to retract the compression member 80 before a firing stroke is completed, for instance in a case where completing the firing stroke may cause tissue to be undesirably cut. Although features such as an articulation lever, a retraction handle, a firing lockout assembly, and an emergency return button are not explicitly illustrated in the device 10, a person skilled in the art will recognize a variety of configurations for each feature that can be incorporated into the handle portion 20 and/or other portions of the device 10 without departing from the spirit of the present disclosure.

Shaft

The shaft 40 can be removably coupled to the distal end 20d of the handle portion 20 at a proximal end 40p of the shaft 40 and can include a bore 42 extending therethrough for passing mechanisms to help actuate the jaws 52, 54, or to perform other functions at the surgical site, such as cutting or delivering electrical energy for sealing. In the described embodiment, the compression member 80 (not shown) and leads 30 are coupled to the components of the handle portion and extend through the shaft 40 to the end effector 50. A distal end 40d of the shaft 40 can be configured to receive the end effector 50 by any known means for coupling an end effector to a shaft, including by a removable connection that allows various end effectors to be removably and replaceably coupled to the distal end 40d. While the shaft 40 can have any number of shapes and configurations, depending, at least in part, on the configurations of the other device components with which it is used and the type of procedure in which the device is used, in the illustrated embodiment the shaft 40 is generally cylindrical and elongate.

End Effector

The end effector can have a variety of sizes, shapes, and configurations. In exemplary embodiments provided for in FIGS. 2A-2C, an end effector 50, 50',50" includes a first jaw 52, 52',52" and a second jaw 54, 54',54" disposed at the distal end 40d of the shaft 40. As shown, the second lower or bottom jaw 54, 54',54" can be coupled to the distal end 40d such that it is relatively fixed with respect to the shaft 40 while the first, upper or top jaw 52, 52',52" can be pivotally coupled to the lower jaw 54, 54',54" to allow the jaws to be opened and closed with respect to each other. For ease of description, each of the components described with respect to FIGS. 2A-2C will be referred to by only the reference numeral not including a prime symbol ('), although the descriptions will be equally applicable to the three embodiments unless indicated otherwise. The appropriate reference numerals, including the prime symbols ('), are provided in FIGS. 2B and 2C.

Figure 2A:
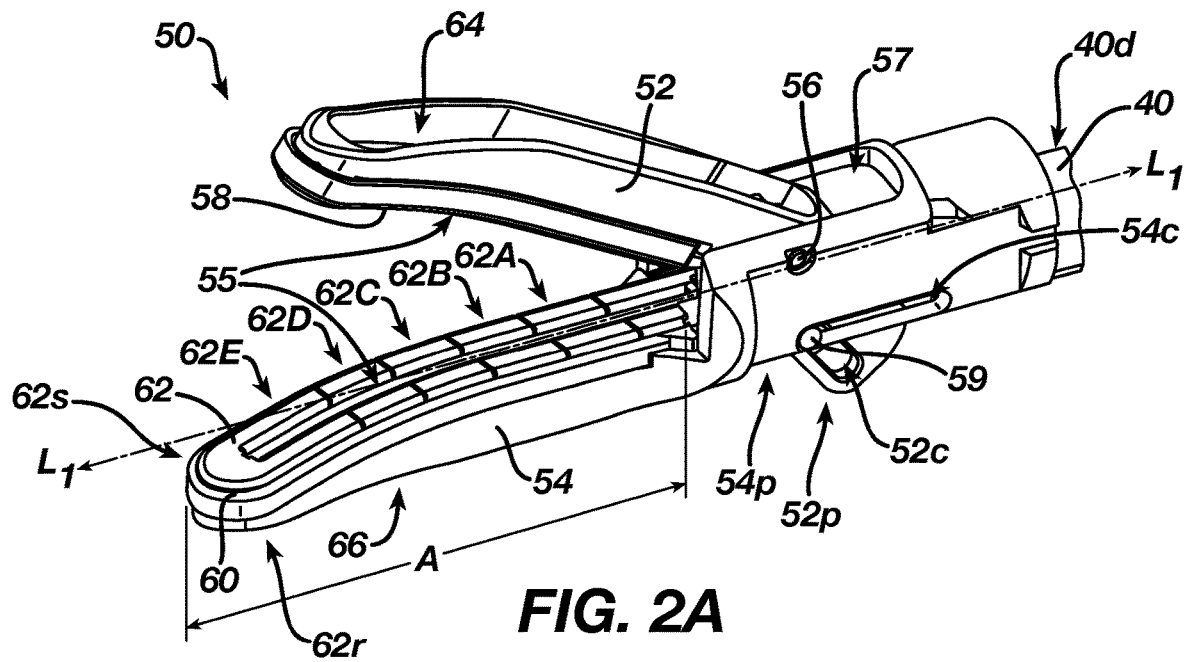
FIG. 2A is a perspective view of one exemplary embodiment of an end effector of the surgical device of FIG. 1, the end effector including an upper jaw and a lower jaw, the lower jaw having an electrode associated therewith, and the electrode having five zones formed therein.
Figure 2B:
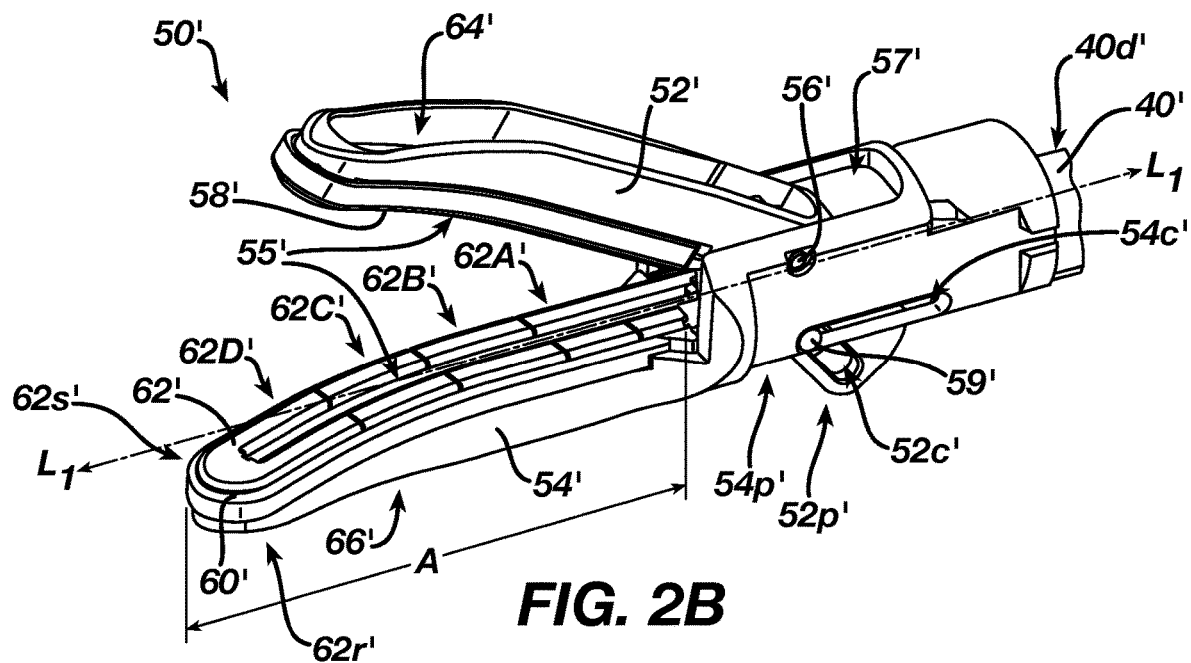
FIG. 2B is a perspective view of another exemplary embodiment of an end effector of a surgical device of the nature of FIG. 1, the end effector including an upper jaw and a lower jaw, the lower jaw having an electrode associated therewith, and the electrode having four zones formed therein.
Figure 2C:
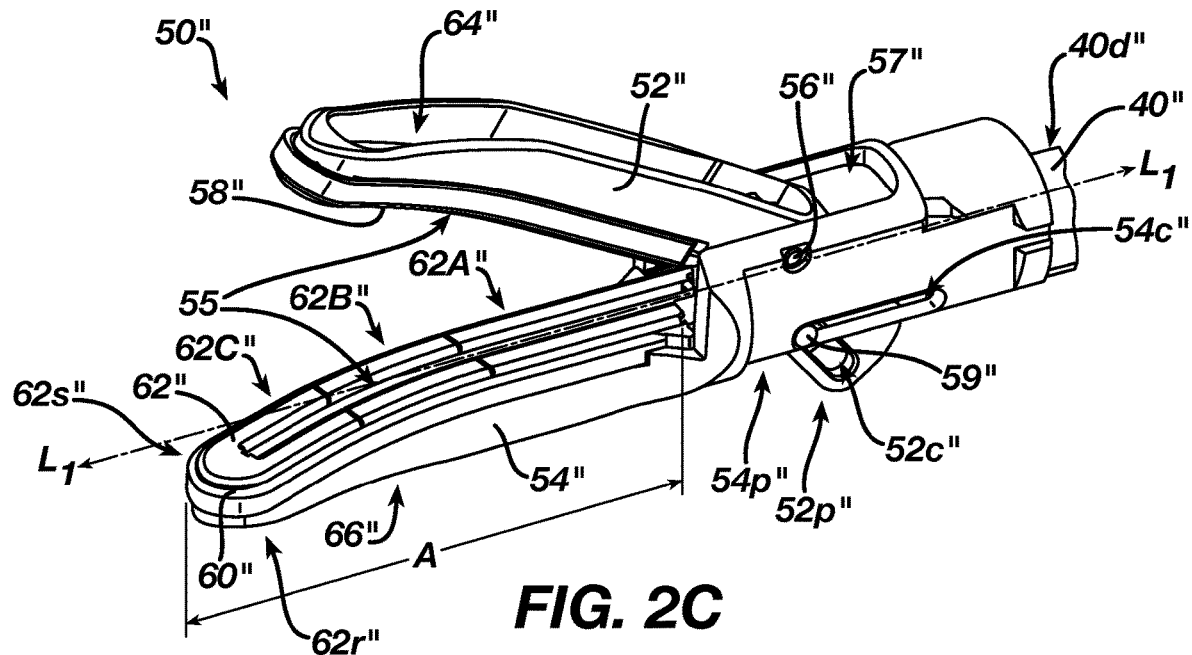
FIG. 2C is a perspective view of still another exemplary embodiment of an end effector of a surgical device of the nature of FIG. 1, the end effector including an upper jaw and a lower jaw, the lower jaw having an electrode associated therewith, and the electrode having three zones formed therein.
Figure 3:
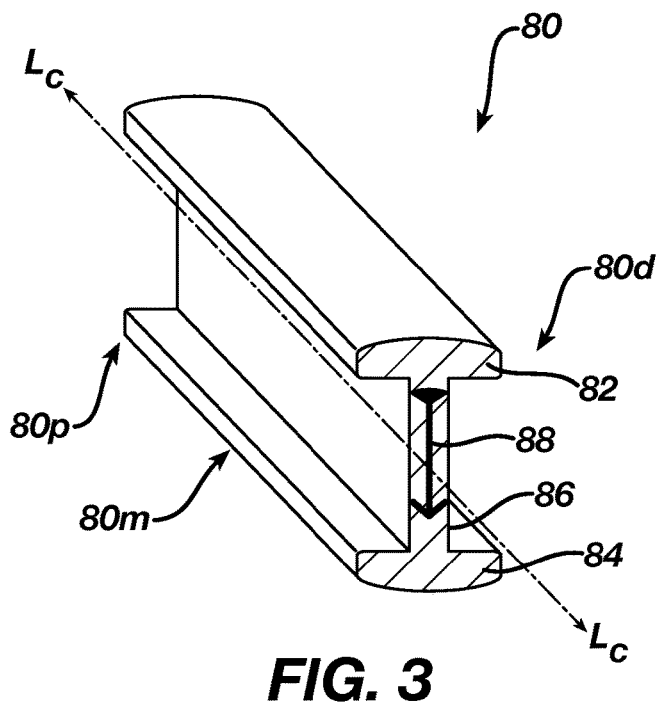
FIG. 3 is a perspective view of a cutting blade mechanism of the surgical device of FIG. 1.

In the illustrated embodiment the upper jaw 52 is configured to pivot about a pivot point 56 disposed at proximal ends 52p and 54p of the jaws 52 and 54 to move between an open position in which the jaws are positioned at a distance apart, as illustrated in each of FIGS. 2A-2C, and a closed position, in which the jaws are substantially opposed such that surfaces thereof are approximately parallel to each other and to the longitudinal axis $L_1$ extending through the shaft 40 and the end effector 50.

As the jaws 52 and 54' move with respect to each other about the pivot point 56, a pin 59 disposed in channels 52c and 54c formed in the proximal ends 52p, and 54p of the jaws 52 and 54, respectively, can move with respect to the channels 52c and 54c. This movement allows the proximal portion of the jaw 52 disposed proximal of the pivot point 56 to move with respect to the jaw 54. Accordingly, in the embodiments shown in FIGS. 2A-2C, as the upper jaw 52 pivots towards the lower jaw 54 about the pivot point 56, the pin 59 can move proximally within the channels 52c and 54c and the proximal end 52p of the upper jaw 52 can move towards an opening 57 formed in the lower jaw 54. A person skilled in the art will recognize that in other embodiments, the lower jaw 54 can pivot while the upper jaw 52 remains substantially stationary, or both jaws 52 and 54 can be pivotable with respect to each other.

In the illustrated embodiment, the jaws 52 and 54 have a substantially elongate shape with a slight curve along the longitudinal axis $L_1$ at distal ends 52d and 54d of the jaws 52 and 54, but a person skilled in the art will appreciate that a variety of other shapes can be used to form the jaws 52 and 54, including jaws that are substantially elongate and substantially straight and configurations that are not necessarily congruent with respect to the opposed jaws across the duration of the length of the jaws. Further, the jaws 52 and 54 can have any suitable axial length A for engaging tissue, where the axial length A is measured along the longitudinal axis $L_1$ of the end effector 50, as shown in FIGS. 2A-2C. The axial length A of the jaws 52 and 54 can also be selected based on the targeted anatomical structure for transection and/or sealing. Still further, the jaws 52 and 54 can also include an elongate channel 55 extending between the two jaws to form a path through which the compression member 80 can traverse. As shown, the elongate channel 55 can be formed in a surface that is opposed to the tissue engaging surfaces 58, 60 of the jaws 52 and 54.

One or both of the surfaces of the upper and lower jaws 52 and 54 can include one or more electrodes disposed on engagement surfaces 58 and 60 of the respective jaws 52 and 54. As shown, an electrode 62 is disposed on the engagement surface 60 of the lower jaw 54. While various configurations of electrodes and other related components of the jaws 52 and 54 are discussed in greater detail below, generally the electrode 62 is configured to supply energy to tissue disposed between the jaws 52 and 54 to coagulate or seal the tissue. The electrode 62 can be coupled to the engagement surface 60 using any manner known to those skilled in the art, including, by way of non-limiting example, using an adhesive in some exemplary embodiments, the electrode can made from a positive temperature coefficient (PTC) polymer or matrix that provides homogeneous and precisely regulated energy delivery with low thermal spread. The PTC conductive-resistive matrix can be a variably resistive body that comprises a polypropylene or a medical grade silicone polymer that is doped with conductive particles carbon). Polymer PTC materials are known in the field of over current protection devices that will "trip" and become resistant when a selected trip current is exceeded. Although in the illustrated embodiments the electrode 62 is associated with only the lower jaw 54, in other embodiments, one or more electrodes can be disposed on only the upper jaw 52 or on both the upper and lower jaws 52 and 54. Likewise, any number of electrodes can be used on either jaw 52 and 54.

In some embodiments, the jaws 52 and 54 can have any combination of features configured to facilitate grasping tissue therebetween. For example, either one or both of the engagement surfaces 58 and 60 of the jaws 52 and 54 can include one or more surface features formed thereon that can help secure the tissue thereon. The surface features can include, by way of non-limiting examples, teeth, ridges, or depressions configured to increase friction between the tissue and the engagement surfaces 58 and 60 without tearing or otherwise damaging the tissue in contact with such surface features. A person skilled in the art will recognize that providing a plurality of teeth along an axial length of both engagement surfaces 58 and 60 can facilitate grasping tissue and forming substantially smooth, uniform layers of tissue to improve tissue effect. Further, the first and second jaws 52 and 54 can include features for interacting with a compression member 80. For example, the first and second jaws 52 and 54 can include first recessed slots 64 and second recessed slots 66 (not visible), respectively, that can be in communication with elongate channel 55, can receive portions of the compression member, and act as a track to direct movement of the compression member.

Compression Member

A compression member can have various sizes, shapes, and configurations. In general, a compression member can have an elongate shape and can be movable proximally and distally along the longitudinal axis $L_1$. An exemplary compression member 80 is illustrated in FIG. 3. As shown, the compression member 80 can have a proximal end 80$p$, a medial portion 80$m$, and a distal end 80$d$. The proximal end 80$p$ and the medial portion 80$m$ of the compression member 80 can be sized and shaped to reciprocate within the shaft 40 of the device 10, while the distal end 80$d$ of the compression member 80 can be sized and shaped to interact with the jaws 52 and 54 of the end effector 50 (or the end effectors 50',50" of FIGS. 2B and 2C as well), for example be traveling through the channel 55 while being disposed between the opposed tissue-engaging surfaces 58 and 60 of the jaws. A longitudinal axis $L_C$ of the compression member 80 can be aligned and coaxial with longitudinal axis $L_1$ of the end effector 50 and of the shaft 40, though other configurations are possible.

The compression member 80 can be actuatable from the proximal handle portion of the instrument by any suitable mechanism that is operatively coupled to the proximal end 80$p$ of the compression member 80, as discussed above. The compression member 80 can include a connecting portion 86 and upper and lower flanges 82, 84, also referred to as ribs, which can extend substantially perpendicular to the connecting portion 86. This configuration can provide an "I-beam" type cross-sectional shape at the distal end 80$d$ of the compression member 80. The upper and lower flanges 82, 84 can be sized and shaped to slide in the recessed slots or tracks 64 and 66 in each of the upper and lower jaw 52 and 54, for instance by sliding along a surface formed in the jaws 52, 54 adjacent to the tracks 64, and this sliding contact of lateral edges of the flanges 82, 84 and sides of each of the recessed slot portions can prevent lateral flexing of the jaws 52 and 54. The compression member 80 can have various other configurations. For example, the upper flange 82 can have a width that is greater than a width of the lower flange 84, the widths being measured in a direction perpendicular to the longitudinal axis $L_1$ of the end effector 50. In addition, the upper and lower flanges 82, 84 can extend along an entire length of the compression member 80, as shown in FIG. 3, or can extend along only a portion of a length of the compression member, e.g., only a distal portion of the compression member.

The device can include a cutting element 88 having a sharp or serrated edge configured to transect tissue captured between the jaws 52 and 54, and the cutting element can be sized and shaped to transect or cut various thicknesses and types of tissue. For example, the cutting element 88 can be a terminal, vertically disposed cutting edge positioned at the distal end 80$p$, the cutting element extending vertically between the first and second jaws 52 and 54. As shown in FIG. 3, the cutting element 88 is formed on the connecting portion 86 of the compression member 80. The cutting element 88 can be coupled to the connecting portion 86 or integrally formed therewith. Alternatively, the connecting portion 86 can itself be a cutting edge. In some embodiments, the cutting element can be recessed relative to distal ends of upper and lower flanges 82, 84 of the I-beam compression member 80 so that compression occurs prior to transecting or cutting of the tissue. In another embodiment, the cutting element can be a knife blade that is not attached to a compression member such that the cutting element can advance and retract relative to the jaws without applying compression to the tissue. In embodiments in which the cutting element is included as part of the compression member, the compression member can also be referred to as a cutting element, cutting blade, or other terms for this type of feature known by those skilled in the art.

A person skilled in the art will recognize that other compression members can be used, or alternatively, the jaws can be closed using other mechanisms known to those skilled in the art that do not involve a compression member. Such embodiments can then include one or more cutting elements configured to advance through jaws and cut grasped tissue. The inclusion of an "I-beam" shape compression member in no way limits the types of jaw closure and tissue cutting elements that can be used in conjunction with the present disclosures.

Furthermore, and more generally, the illustrated embodiment of a surgical device 10 provides one of many different configurations, and associated methods of use, that can be used in conjunction with the disclosures provided herein. A variety of other configurations of a surgical device are also possible. For example, in some embodiments the device can be configured to apply staples to tissue in addition to or in lieu of either or both of cutting or sealing features. Some, non-limiting examples of other device configurations that can be used in conjunction with the present disclosure, and their related methods of use, include the disclosures provided for in U.S. Pat. No. 8,298,232, U.S. Patent Application Publication No. 2012/0083835, and U.S. Patent Application Publication No. 2013/0161374, each of which is incorporated by reference herein in its entirety.

Segmented Electrode(s)

As shown in FIGS. 2A-2C, the electrode 62, 62',62" affixed to the tissue engagement surface 60, 60',60" on the lower jaw 54, 54',54" can have two or more zones formed therein (identified by letters) by segmenting the electrode. The device in FIG. 2A includes 5 zones: 62A, 62B, 62C, 62D, 62E; the device in FIG. 2B includes 4 zones: 62A, 62B, 62C, and 62D; and the device in FIG. 2C includes 3 zones: 62A, 62B, and 62C. Other numbers of zones are possible. The zones can be formed using any techniques known to those skilled in the art for forming a cut in an electrode, including but not limited to laser etching lines in the electrode 62, 62',62" to form each zone. The zones can be any size and shape, and can differ in size and shape across the length of the electrode. Accordingly, although in the embodiment illustrated in FIG. 2A, the first three zones 62A, 62B, and 62C are approximately equal in length and the two distal-most zones 62D and 62E are longer than the first three zones, any other configurations can be formed in the electrodes. Further, although the cuts formed each section are approximately aligned on opposed sides 62r, 62r', 62r" and 62s, 62s', 62s" of the electrode 62, 62',62", they can be staggered along the surface of the electrode to create any desired size, shape, and number of zones. As shown, the opposed sides 62r, 62r', 62r" and 62s, 62s', 62s" are formed by the channel 55, 55',55" formed in the lower jaw 54, 54',54". Still further, while the present disclosure describes a single electrode having cuts formed therein to create multiple zones, in other embodiments multiple electrodes can be provided with the individual electrodes defining a particular zone, or the individual electrodes having cuts formed therein to further define additional zones even more specific than the initial zone formed by the individual electrode.

Each zone can include a parameter monitor. The parameter monitor can be configured to measure a parameter that is commensurate with a thickness of tissue. For example, parameter monitors can be configured to measure impedance within the zone, which can be used to identify the thickness and/or type of tissue located within the zone. As used herein, impedance is generally considered a parameter of the tissue, while the thickness of the tissue, or the identification of the type of tissue, that is tied to that measured impedance is generally considered a characteristic of the tissue. Higher impedances can typically be associated with thicker tissue or other, thicker objects, such as arteries or veins, while lower impedances can typically be associated with thinner tissue or other, thinner objects. Not only do the parameter monitors allow for the measurement of the parameter, they also allow the measurement to be tied to a more specific location. Thus, as a thickness of tissue or other objects disposed in the jaw changes over the length of the jaw, the parameter monitors can identify where within the jaw assembly the thicker and thinner tissues or objects are located. This allows other functions to be controlled and adjusted at a more precise, local level. For example, the speed of a compression member or cutting element can be adjusted based on the thickness of tissue/objects at particular locations along the length of the jaw assembly. Likewise, electrodes can be turned on and off, and used for desired, varying lengths of time when they are turned on based on the thickness of tissue/objects at particular locations along the length of the jaw assembly.

Figure 4A:
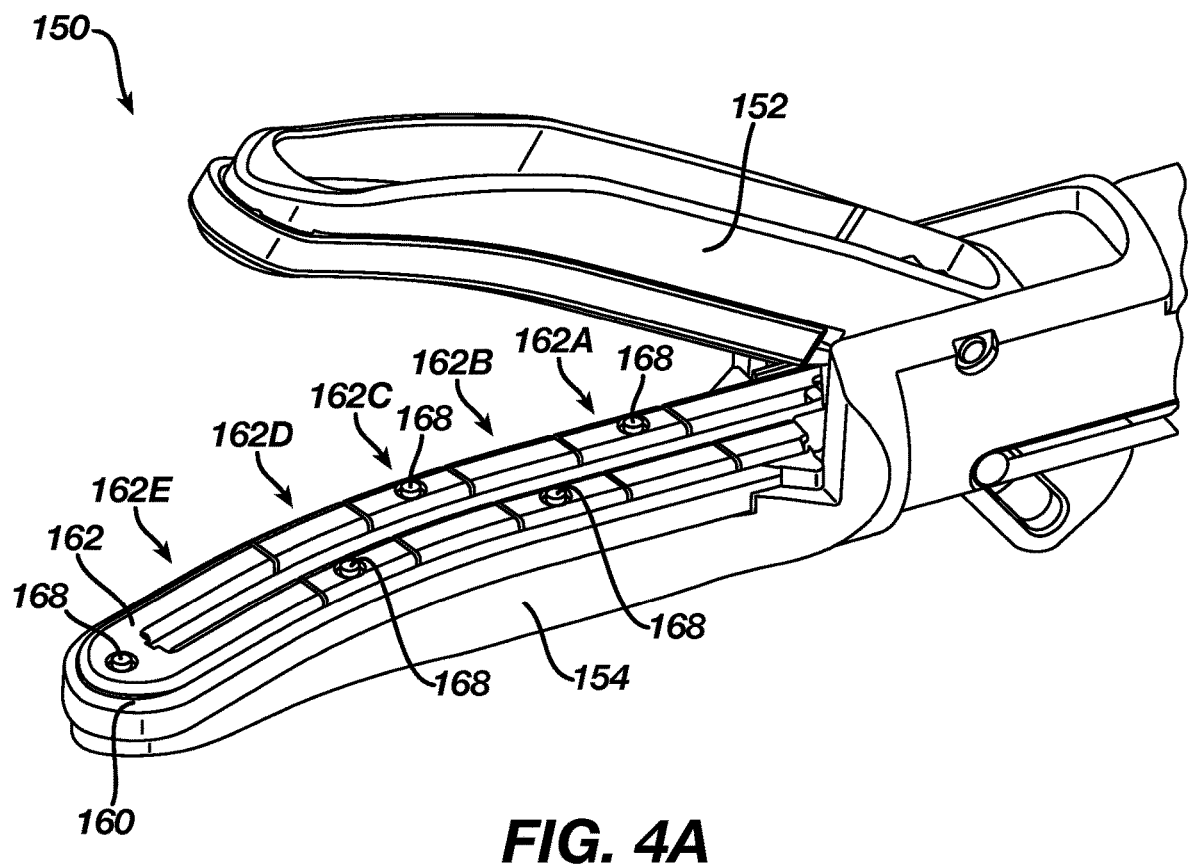
FIG. 4A is a perspective view of another exemplary embodiment of an end effector of a surgical device of the nature of FIG. 1, the end effector including an upper jaw and a lower jaw, the lower jaw having an electrode associated therewith, the electrode having five zones formed therein, and the end effector also including at least one stand-off disposed in each zone.

In one exemplary embodiment of an end effector 150 provided for in FIGS. 4A and 4B, each zone 162A, 162B, 162C, 162D, and 162E of an electrode 162 coupled to a tissue engaging surface 160 of a lower jaw 154 includes one conductive stand-off or protrusion 168 extending from the lower jaw 154, through the electrode 162, and extending vertically away from the electrode 162, towards an upper jaw 152. In exemplary embodiments, each stand-off or protrusion 168 is electrically isolated with respect to the other stand-offs or protrusions 168. In an alternative embodiment, provided for in FIG. 4C, the stand-offs are replaced with more general sensors 168' disposed on an electrode 162' and configured to measure one or more parameters, such as impedance. As shown, for the lower jaw 154', each of the four most proximal zones 162A', 162B', 162C', and 162D' include a single sensor 168', and the distal-most zone 162E' includes two sensors 168'. Any number of stand-offs or sensors can be provided in any one zone provided there is space for them within that zone. The stand-offs can be made of a variety of materials, including but not limited to electrically conductive materials. Some exemplary electrically conductive materials for use in forming stand-offs include but are not limited to one or more metals or metal alloys, such as titanium and stainless steel. Each stand-off 168 can be used to measure an impedance in its respective zone by sending a pulse to the upper jaw 152 when the electrode 162 is off, as illustrated schematically by FIG. 4B, and then measuring the length of time it takes for that pulse to reach the upper jaw 152. The stand-offs 168 can also be effective to prevent unnecessary damage to the electrode 162 by engaging a tissue engagement surface 158 of the upper jaw 152 and thus preventing direct contact between the tissue engagement surface 158 and the electrode 162. The illustration in FIG. 4C likewise schematically illustrates the use of the sensors 168' in each zone to measure a parameter for that zone, diagraming which sensors provide information for which zones.

A person skilled in the art will recognize various parameters that can be measured using various types of sensors, including sensors capable of measuring impedance. Further, a person skilled in the art will recognize that other parameters besides impedance can be measured by the stand-offs 168 and sensors 168', and thus other types of parameter monitors besides stand-offs 168 and sensors 168', can be used to measure a tissue characteristic such as tissue thickness based on the measured parameter. Likewise, other characteristics related to the tissue or its environment can be used to evaluate the tissue. By way of non-limiting examples, temperature sensors and optical sensors can be used in conjunction with the disclosures provided for herein to monitor one or more parameters and/or characteristics related to a grasping, cutting, and/or sealing surgical procedure. By way of non-limiting example, one or more Hall Effect sensors could be included as part of the jaw assembly to measure a gap between the upper and lower jaws. By way of further non-limiting example, an optical sensor capable of measuring translucency of an object can be included as part of the jaw assembly to help make tissue type and thickness determinations. A person skilled in the art, in view of the present disclosures, will recognize that other types of electrically-based measurements are also possible without departing from the spirit of the present disclosures, including measurements that enable the comparison of the difference of a particular parameter at different locations throughout the jaw assembly (i.e., its delta Δ). Further, in some embodiments, the electrodes themselves can be used to measure one or more parameters, including impedance.

In addition to using the individual zones for purposes of mapping a particular parameter, e.g., impedance, or a particular characteristic, e.g., tissue thickness, at different locations across the length of the jaw assembly, the zones can also be used to selectively apply energy to tissue disposed therein. In particular, the circuitry of the device can be such that energy supplied by the electrode to tissue disposed in the jaw assembly can be selectively turned on and off at each individual zone. Accordingly, one or more zones, or even portions of the zones if so configured, can be activated to apply energy to tissue while at the same time one or more zones, or portions thereof, remain inactive. The ability to selectively turn on and off electrodes can also be useful to measure one or more parameters in a particular zone, as in some exemplary embodiments the electrodes are turned off prior to making a parameter measurement, e.g., prior to sending a pulse from one or more of the stand-offs 168.

In some embodiments, the electrode itself, or a parameter monitor associated therewith, can identify a short within a particular zone. A short can be indicative of opposing electrodes of the jaw assembly being closed on a conductive member such as a surgical staple line or a clip, as opposed to being closed on tissue alone. The electrode or parameter monitor can then communicate the existence of the short within one or more of the particular zones and treatment can be adjusted accordingly.

As discussed earlier, although the present disclosure provides for an electrode on the lower jaw, other configurations can include a jaw assembly having an electrode on the upper jaw in lieu or in addition an electrode being associated with the lower jaw. An electrode associated with the upper jaw can also be segmented into a plurality of zones as described herein, or can have other configurations for electrodes provided for herein or otherwise known to those skilled in the art.

FIGS. 5A-5E illustrate various schematic illustrations of tissue disposed in jaw assemblies to demonstrate the identification and mapping of zones in accordance with the present disclosures. Each figure provides a schematic illustration of tissue disposed between the jaws, i.e., the illustrations are not of the actual tissue itself, to illustrate a length of the tissue with respect to the length of the jaw assembly. Generally, unless the tissue is incredibly thick, the jaws would be disposed closer together when determining its thickness than provided for in the illustrated embodiments.

Figure 5A:
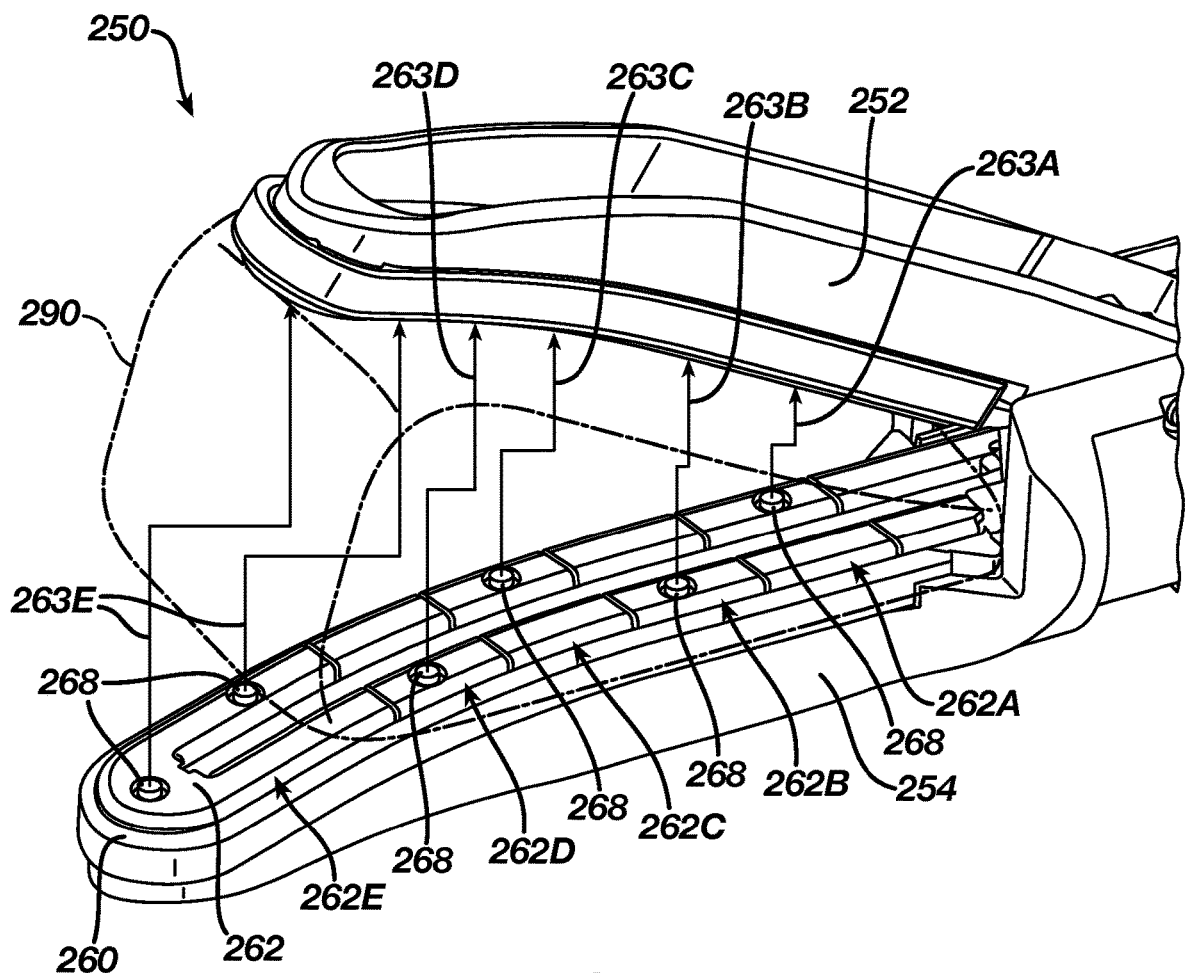
FIG. 5A is a perspective view of an end effector of the nature of FIG. 4A, the end effector including an upper jaw and a lower jaw, the lower jaw having an electrode associated therewith, the electrode having five zones formed therein, and the end effector also including at least one sensor disposed in each zone, the illustration further including a schematic representation of where tissue is disposed between the lower jaw and the upper jaw and indications of pathways from the sensors to the upper jaw.

As shown in FIG. 5A, an end effector 250 includes an upper jaw 252 and lower jaw 254 with an electrode 262 disposed on a tissue engaging surface 260 of the lower jaw 254. The electrode 262 is divided into five zones 262A, 262B, 262C, 262D, 262E, with the four proximal-most zones 262A, 262B, 262C, and 262D having one stand-off 268 disposed therein and the distal-most zone 262E having two stand-offs 268 disposed therein. A representation of tissue 290 is provided between the two jaws 252, 254, and as shown the representation of tissue 290 extends across all five zones 262A, 262B, 262C, 262D, and 262E. Accordingly, when the electrode 262 is switched off so that it is not part of a current path extending between the two jaws 252, 54, and instead is isolated from current power supplied by a driver, a pulse is provided by the stand-offs 268 that passes through tissue disposed between the jaws 252, 254 and reaches the upper jaw 252, as illustrated by arrows 263A, 263B, 263C, 263D, and 263E, respectively. Based on the time it takes the pulse to travel through the tissue to the upper jaw 252, an impedance value for that zone is determined, which then correlates to a thickness of the tissue disposed in that zone. A measurement can be performed by each stand-off 268, and thus in the illustrated embodiment a determination of tissue thickness can be made for each of the five zones 262A, 262B, 262C, 262D, and 262E, with two determinations being able to be made in the distal-most zone 262E. The ability to make two measurements in the distal-most zone 262E can be advantageous because, as shown, this zone is larger than the other four zones 262A, 262B, 262C, and 262D, so it provides for more precision within a single zone.

Figure 5B:
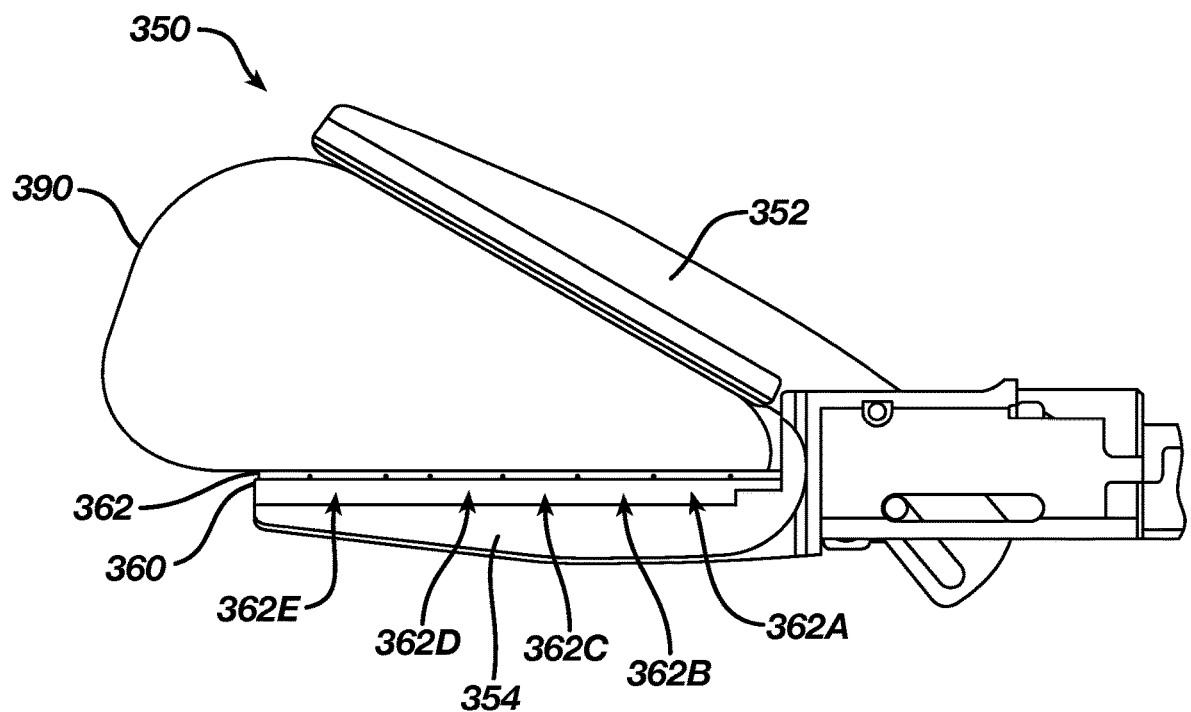
FIG. 5B is a side view of the end effector of FIG. 2A having a schematic representation of where tissue is disposed between the lower jaw and the upper jaw, the tissue being disposed in each of the five zones.

FIG. 5B similarly illustrates an end effector 350 having an upper jaw 52 and lower jaw 354 with an electrode 362 disposed on a tissue engaging surface 360 of the lower jaw 354. The electrode 362 is likewise divided into five zones 362A, 362B, 362C, 362D, 362E, and a parameter monitor (not shown) can be disposed in each zone. Each parameter monitor can be configured to identify the presence of tissue in the zone in which the parameter monitor is disposed, as well as an impedance value, tissue thickness, or other parameter or characteristics for the zone in which the parameter monitor is disposed. A map can then be communicated to a controller. The map can take any form known to those skilled in the art provided it communicates the essential information to the controller, including the location of the tissue (e.g., which zone, or if multiple monitors in each zone, a more specific location with a zone) and the impedance value or thickness of the tissue (or other parameter or characteristic if another parameter or characteristic of the tissue or its environment is measured). In the illustrated embodiment, because the representation of tissue 390 is disposed in all five zones 362A, 3629, 362C, 362D, 362E, the resulting map would indicate the presence of tissue in each of the five zones, as well as an impedance value and/or thickness of tissue at each zone.

Figure 5C:
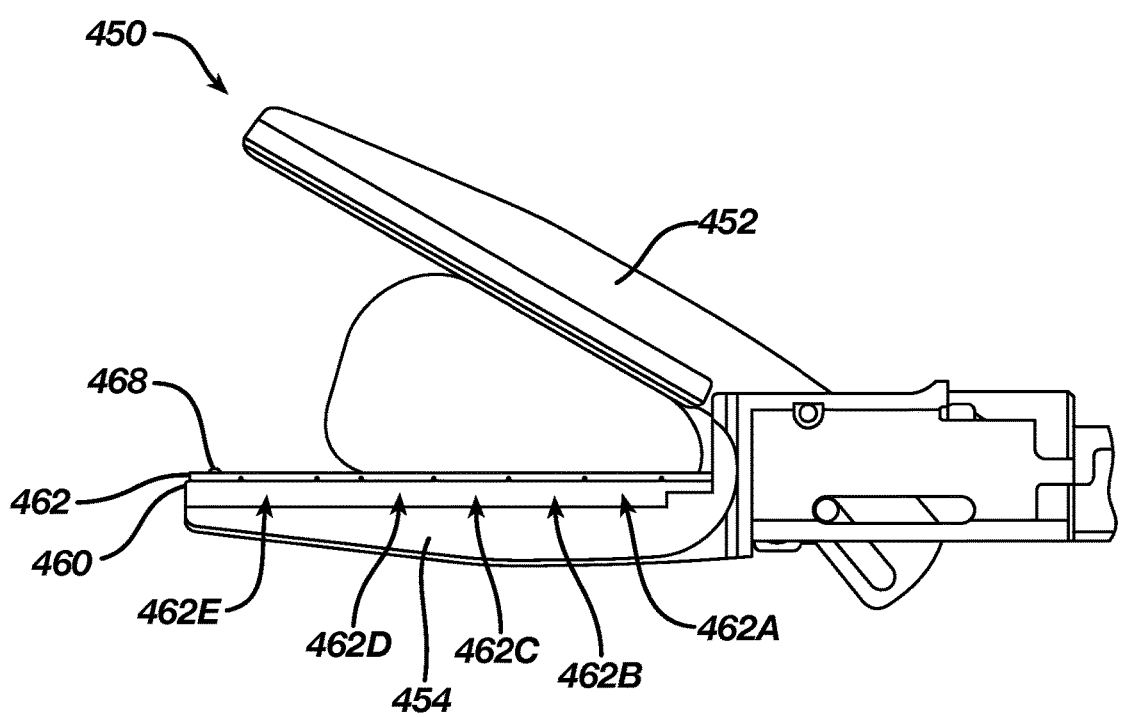
FIG. 5C is a side view of the end effector of FIG. 2A having a schematic representation of where tissue is disposed between the lower jaw and the upper jaw, the tissue being disposed in four of the five zones.
Figure 5D:
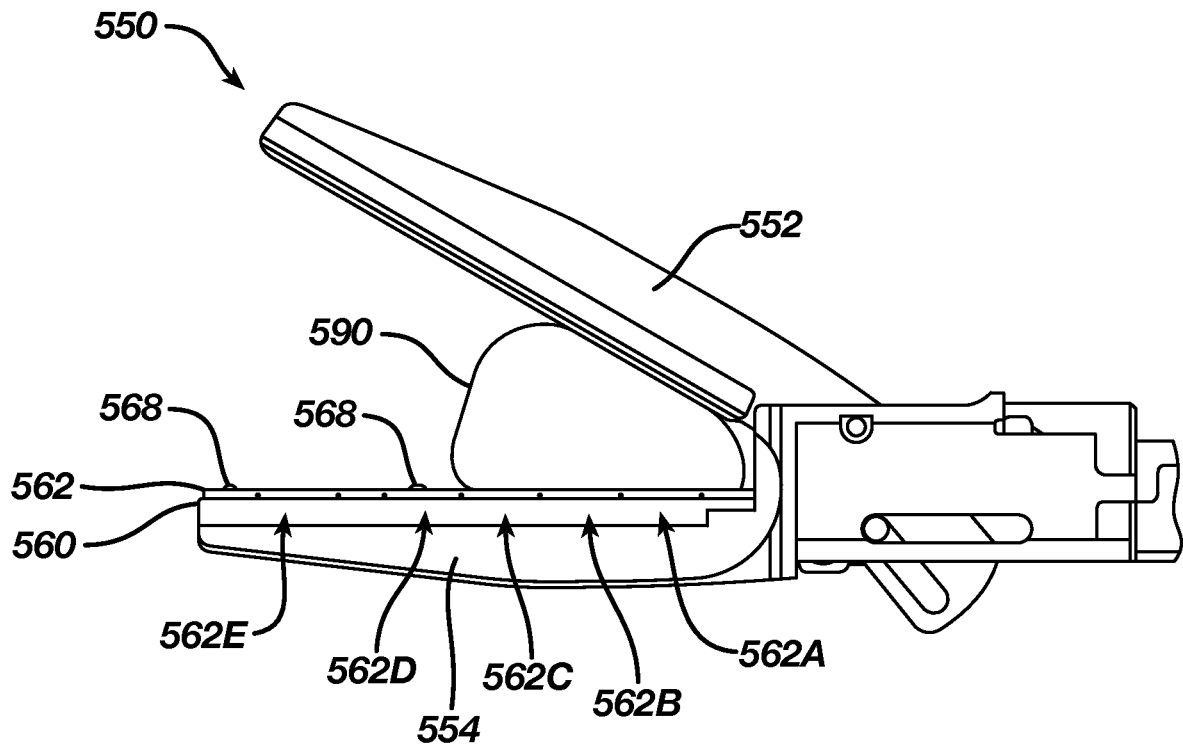
FIG. 5D is a side view of the end effector of FIG. 2A having a schematic representation of where tissue is disposed between the lower jaw and the upper jaw, the tissue being disposed in three of the five zones.
Figure 5E:
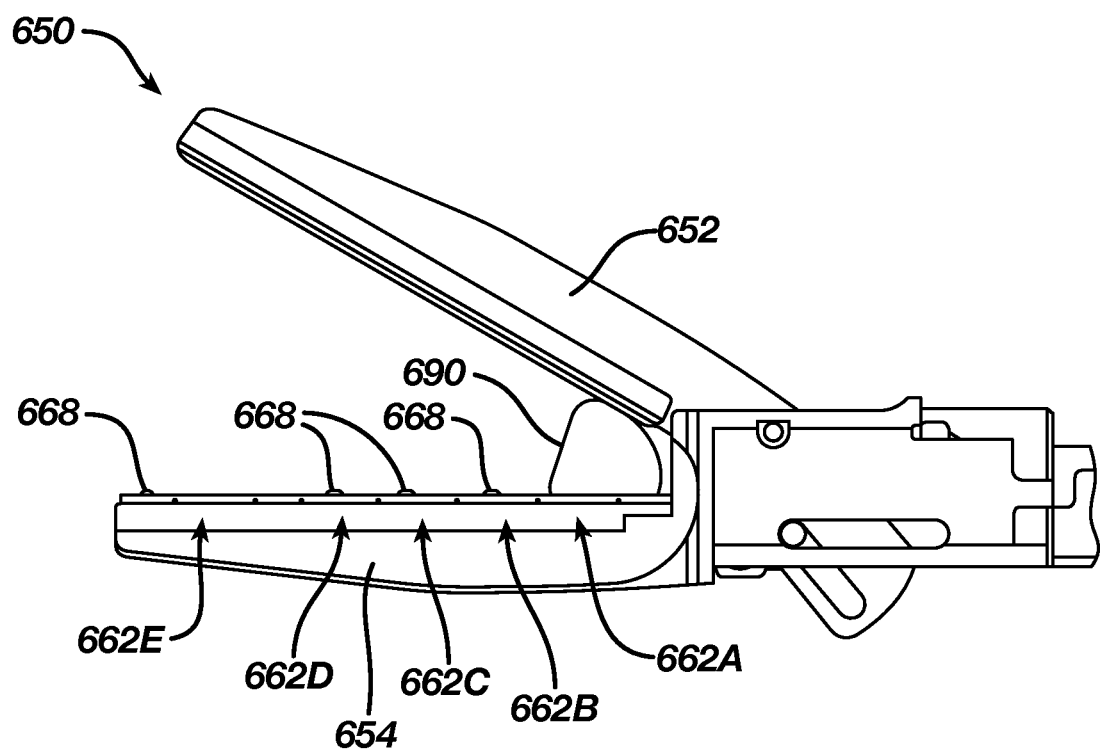
FIG. 5E is a side view of the end effector of FIG. 2A having a schematic representation of where tissue is disposed between the lower jaw and the upper jaw, the tissue being disposed in one of the five zones.

FIGS. 5C-5E illustrate three further embodiments in which a representation of tissue 490, 590, 690 is provided to illustrate a presence of tissue in particular sections of the end effectors 450, 550, 650. The embodiment provided for in FIG. 5C illustrates that the tissue disposed between the jaws 452 and 454 is present in the four proximal-most zones 462A, 462B, 462C, and 462D, and is not present with any significance in the distal-most zone 462E, which is why a stand-off 468 is visible in the distal-most zone 462E. The embodiment provided for in FIG. 5D illustrates that the tissue disposed between the jaws 552 and 554 is present in the three proximal-most zones 562A, 562B, and 562C but is not present with any significance in the two distal-most zones 562D and 562E, which is why a stand-off 568 is visible in each of zones 562D and 562E. The embodiment provided for in FIG. 5E illustrates tissue in just the proximal-most zone 662A, with each of the second, third, fourth, and fifth zones 662B, 662C, 662D, and 662E being free from tissue, and thus having their respective stand-offs 668 visible in the illustration.

The timing as to when the tissue parameter is measured in comparison to the location of the jaws with respect to each other can depend, at least in part, on the parameter being measured, the amount of compression the user plans to apply to the tissue with the jaws when the tissue is being cut and/or sealed, and more generally the type of procedure being performed, among other factors. While the portions representing the tissue are not intended to be tissue themselves, generally, parameter measurements can be taken when the tissue-engaging surfaces of the jaws are in contact with the tissue but no significant amount of force is applied to the tissue. For example, no force greater than approximately 30 Newtons is applied to the tissue disposed between the jaws, or in some embodiments no force greater than approximately 26.6 Newtons. Such force thresholds are in no way intended to be limiting, and thus thresholds greater than approximately 30 Newtons and less than approximately 26.6 Newtons are possible. In other embodiments, the tissue may be more tightly grasped before measuring a parameter, such as impedance, is determined.

System in Use

In use, the surgical device 10 can be disposed in a cannula or port and disposed at a surgical site. A tissue to be cut can be placed between the jaws 52, 54 of the surgical device 10. Features of the device 10, such as the rotating knob 32 and an actuation lever to articulate an end effector (if provided), can be maneuvered as desired by the clinician to achieve a desired location of the jaws 52, 54 at the surgical site and the tissue with respect to the jaws 52, 54. After appropriate positioning has been achieved, the trigger 24 can be pulled toward the stationary handle 26 to actuate the firing system. The trigger 24 can cause components of the firing system to operate to cause the upper jaw 52 to advance towards the lower jaw 54 to clamp the tissue disposed therebetween. More particularly, the firing system can actuate the compression member 80 and cause the flanges 82, 84 to slide through channels 64, 66 of the jaws 52, 54, for example by sliding along surfaces formed in the jaws 52, 54 within the channels 64, 66, which in turn advance the jaws 52, 54 towards each other. As the first stroke comes to completion, the jaws 52, 54 can move to a fully closed position in which the tissue engaging surfaces, in the illustrated embodiment of FIG. 2A, the surface 58 and the electrode 62, grasp tissue extending therebetween.

In some embodiments, a first firing of the trigger 24 can cause the jaws 52, 54 to clamp the tissue, while subsequent firings of the trigger 24 can cause the compression member 80 to be advanced distally through at least a portion of the end effector 50. A single, subsequent firing can fully advance the compression member 80 through the jaws 52, 54, or alternatively, the components in the handle portion 20 can be configured such that multiple, subsequent firings are required to fully advance the compression member 80 through the jaws 52, 54. In other exemplary embodiments, a driver disposed within the handle portion 20 and associated with a firing trigger can actuate the compression member 80 automatically in response to activation of the firing trigger 24.

Figure 6:
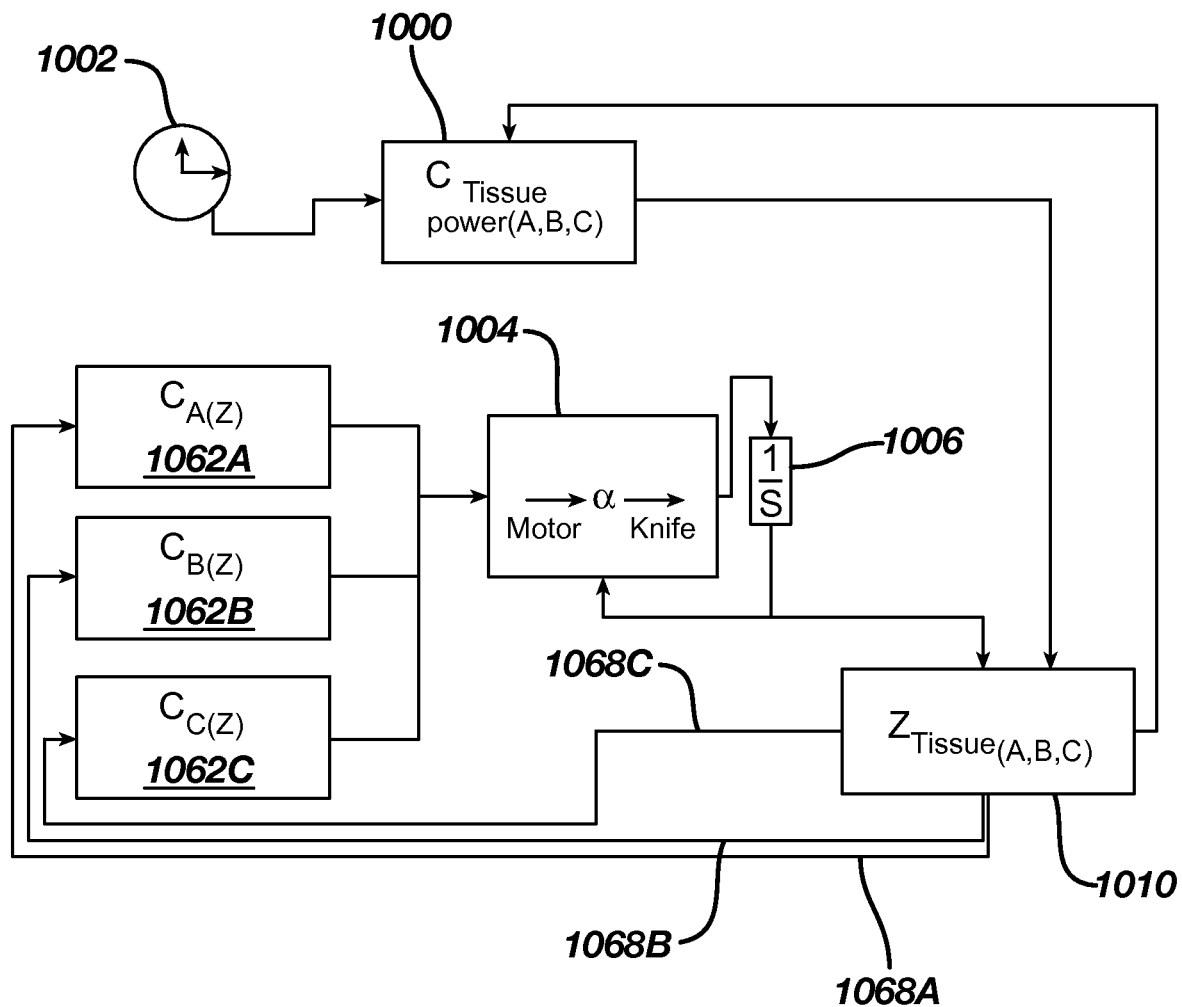
FIG. 6 is a schematic illustration of a circuit for use in conjunction with a surgical device of the nature of FIG. 1.

The speed of the compression member 80 can be based, at least in part, on feedback provided by the information mapped about the various zones provided in the electrode 62. The feedback allows for real time adjustments to be made to the speed of the compression member. FIG. 6 provides one exemplary embodiment of a feedback loop associated with an electrode having three zones.

As shown, a controller 1000 for monitoring measured parameters and responding to the same is provided. The controller 1000 can be part of the device itself, for example a component of the handle portion 20, or it can be an outside component that can be plugged into the device. In embodiments in which a motor is provided as part of the handle portion 20 but a controller 1000 is not, the controller 1000 can be plugged into the device 10 in conjunction with a power source that is provided to power the motor. As illustrated by the circle component 1002 in the schematic diagram, the controller 1000 can be configured to look for feedback related to a particular parameter, e.g., impedance, after a certain amount of time or when a certain amount of power is provided. The controller 1000 can be wired to parameter monitors 1068A, 1068B, and 1068C associated with each zone 1062A, 1062B, and 1062C of the electrode 1062 to power the monitors 1068A, 1068B, and 1068C and receive feedback from the same. In the illustrated embodiment, the controller 1000 provides power to each of the three zones 1062A, 1062B, and 1062C. When jaws of the device are closed on tissue, the electrode can be part of a current path extending between the two jaws. To measure impedance, this current path can be broken such that each parameter monitor 1068A, 1068B, and 1068C is isolated, after which time the parameter monitors can send a pulse from the monitor 1068A, 1068B, and 1068C disposed on one jaw, through the tissue 1010, and to the other jaw. The time it takes the pulse to travel can then be communicated back to the controller 1000, with the controller 1000 accepting measurements from each of the three parameter monitors 1068A, 1068B, and 1068C.

The controller 1000 then maps information related to the tissue 1010 with respect to the zones. Thus, if zone 1062A indicates the tissue 1010 is thicker than the tissue 1010 in zone 1062B and that there is no tissue in zone 1062C, the controller 1000 maps this information for use. Likewise, as indicated above, whether or not a short exists within a particular zone can also be identified by the system and communicated to the controller for mapping purposes. Based on the feedback provided from the parameter monitors 1068A, 1068B, and 1068C, the controller 1000 can then adjust a speed of the motor in real time, and thus the speed of the compression member 80 because the speed of the compression member can be proportional to the speed of the motor, as shown at box 1004 of the diagram. Accordingly, in the embodiment described above in which the tissue 1010 is thicker in zone 1062A than in zone 1062B, and the tissue 1010 is not disposed in zone 1062C, the controller 1000 can slow the speed of the compression member 80 to cut the tissue 1010 in zone 1062A and then speed it up to cut the tissue 1010 in zone 1062B. The controller 1000 can then instruct the compression member 80 to not travel through zone 1062C since there is no tissue disposed there. This type of local control in real time provides for more efficiency and accuracy in the cutting, and a better product because the cut speed can be based on the thickness at particular locations along the length of the jaw assembly.

Not only can the controller 1000 map the zones formed in the electrode 1062, but it can also be used to determine a location of the compression member 80 with respect to the zones 1062A, 1062B, and 1062C. For example, the controller 1000 can also perform an integration, as illustrated at box 1006 of the diagram, to determine the amount of displacement of the compression member 80, which in turn identifies the location of the compression member 80 with respect to the mapped zones 1062A, 1062B, and 1062C. In other embodiments, sensors can be used to determine the location of the compression member 80 with respect to the end effector.

As discussed, by knowing the thickness of tissue in the end effector and the location of various thicknesses across the length of the end effector, more precise, individualized control can be achieved in real time. In the example discussed above, the compression member 80 could be stopped before reaching the distal end of the end effector because there was no tissue located in the distal-most zone 1062C. In alternative embodiments, the end effector may be used to grasp tissue only at its tip. In such an instance, the controller 1000 can advance the compression member 80 quickly through the zones leading up to the distal end that do not have tissue disposed therebetween before slowing the compression member so it is able to travel at a speed commensurate with the thickness of the tissue grasped at the distal end of the jaws.

The information mapped by the controller 1000 can also be used to selectively apply energy to the grasped tissue 1010 for sealing or coagulating based on the real time feedback provided by the parameter monitors. For example, the controller 1000 can prevent portions of electrodes in zones where no tissue is disposed therein from being turned on to apply energy in that specific zone, thus saving time and energy, and reducing any known risks associated with applying energy to an electrode that is not in contact with tissue 1010 to be sealed. Further, when tissue 1010 is disposed at a particular zone, the amount of energy applied by the electrode in that particular zone can be adjusted in real time based on the tissue thickness. How that energy is adjusted can depend on a variety of factors, including but not limited to the desired end result for the treated tissue 1010, and the combination of the amount of power supplied and length of time for which the power is to be supplied to the tissue 1010. In some instances, for thicker tissue a user may want the controller 1000 to dictate a high amount of energy be used for a short duration of time as opposed to a lower amount of energy for a longer duration of time. Likewise, as the tissue is thinner, the controller 1000 can be configured to apply a lower dose of energy and/or apply it for a shorter period of time. The ability to selectively apply different amounts of energy at different locations across the length of the tissue 1010 allows tissue of various thickness, as well as multiple types of tissue, to be treated without having to re-grasp the tissue. Furthermore, the zones of the electrodes, or the electrode as a whole, can be selectively switched on and off for various functions. For example, typically the electrode is part of the current path that extends from the lower jaw to the upper jaw when it is turned on, but then it is turned off to isolate the electrode from current power supplied by the driver. When it is turned off, the parameter monitor can be operated to make determinations of parameters and/or characteristics of the tissue. Turning the electrode on and off can result in an increased current density. Increasing the current density can be desirable, for example, when sealing or coagulating thicker types of tissue. A person skilled in the art will recognize that the energy for treating the tissue 1010 can be applied before, during, or after the compression member is advanced to cut the tissue 1010, but typically before the compression member is retracted and the tissue 1010 released.

In some embodiments, for instance when the value of impedance for tissue disposed in the jaw assembly is low, power can be cycled to the electrodes at each zone to apply higher concentrated energy within each zone until a threshold impedance value is achieved. This can allow the tissue to be more effectively treated based on the measured parameter within each zone by tailoring the amount of energy applied to the tissue and/or the length of time the energy is applied to the tissue within each respective zone. Once the threshold impedance value is achieved for a particular zone, treatment for that zone can be skipped during the next cycle until the desired impedance value is achieved for each zone.

Turning back to movement of the compression member 80, after the compression member 80 has been advanced distally, the compression member 80 can be retracted back towards its initial position. In some configurations, the compression member 80 can be retracted prior to fully advancing the compression member 80 through the cartridge, for instance embodiments in which the controller 1000 determines there is no tissue disposed in the distal-most zone 1062C. In other embodiments retraction of the compression member 80 can be automated to occur after a predetermined action. For example, once the compression member 80 has distally advanced to its desired location, the subsequent return of the trigger 80 back to a biased open position can cause the compression member 80 to automatically retract. In some embodiments a retraction knob or the like can be included to assist in retracting the compression member, while in other embodiments a motor and associated components can be used to retract the compression member 80. Further, as discussed above, other features, such as a firing lockout mechanism, an anti-reverse clutch mechanism, and an emergency return button, can be relied upon during operation of the surgical device 10, as would be understood by those skilled in the art.

The illustrated embodiment of a surgical device 10 provides one of many different configurations, and associated methods of use, that can be used in conjunction with the disclosures provided herein. Additional exemplary embodiments of devices such as surgical staplers, components thereof, and their related methods of use, that can be used in accordance with the present disclosure include those devices, components, and methods are known to those skilled in the art, and include the patents and patent application publications incorporated by reference above.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a proximal handle portion having a driver;
   an elongate shaft extending distally from the handle portion;
   a jaw assembly having a first jaw and a second jaw pivotally coupled thereto, the first jaw having a tissue-engaging surface that is opposed to a tissue-engaging surface of the second jaw, and at least one of the tissue-engaging surfaces of the first and second jaws including an electrode segmented into a plurality of zones, the plurality of zones being disposed in series between a proximal end of the jaw assembly and a distal end of the jaw assembly, each zone being configured to apply energy supplied by power from the driver to tissue disposed between the first and second jaws to seal the tissue, a protrusion at each zone and extending toward the other of the tissue-engaging surfaces and configured to contact the other of the tissue-engaging surfaces to prevent contact between the electrode and the other of the tissue-engaging surfaces, each protrusion being configured to measure a parameter that is commensurate to a thickness of tissue disposed between the first and second jaws;
   a cutting blade having a distal portion disposed between the opposed tissue-engaging surfaces of the first and second jaws, the distal portion including a terminal, vertically disposed cutting edge that extends vertically between the first and second jaws, the cutting blade translating distally and proximally through the first and second jaws in response to power supplied by the driver; and
   a controller configured to control power output by the driver to adjust a speed of the cutting blade being configured to translate through the first and second jaws and an amount of energy applied by one or more zones of the plurality of zones of the electrode in response to the parameter measured by the protrusion, the controller being configured to be capable of changing the speed of the cutting blade as the cutting blade enters each of the plurality of zones arranged in series,
   wherein each electrode is configured to be switched from an on configuration to an off configuration such that energy is not delivered to the electrode when in the off configuration, and the corresponding protrusion is configured to measure the parameter only when each electrode is in the off configuration.

2. The device of claim 1, wherein each protrusion is configured to measure tissue impedance.

3. The device of claim 2, wherein each protrusion comprises a metal protrusion that is electrically isolated with respect to the other protrusions.

4. The device of claim 3, wherein each metal protrusion is configured to send a pulse to the opposed jaw to measure tissue impedance at the zone in which the protrusion is located.

5. The device of claim 4, wherein the electrode is configured to be selectively switched from being part of a current path extending between the first and second jaws when the jaws are in a closed position, to being isolated from current power supplied by the driver.

6. The device of claim 1, wherein the plurality of zones is at least three.

7. The device of claim 1, wherein the distal portion of the cutting blade further comprises a first rib extending perpendicular to the terminal, vertically disposed cutting edge and disposed in a track formed in a surface of the first jaw that is opposed to the tissue-engaging surface of the first jaw, and a second rib extending perpendicular to the terminal, vertically disposed cutting edge, opposed to the first rib, and disposed in a track formed in a surface of the second jaw that is opposed to the tissue-engaging surface of the second jaw.

8. The device of claim 1, wherein each protrusion extends from the first or second jaw and through the corresponding zone of the electrode without contacting the electrode, and each protrusion is electrically isolated with respect to the other protrusions.

9. A surgical device, comprising:
   a proximal handle portion having a motor disposed therein;
   an elongate shaft extending distally from the handle portion;
   a lower jaw coupled to a distal end of the elongate shaft, the lower jaw having a tissue-engaging surface that includes an electrode segmented into a plurality of zones, and a channel formed in the tissue-engaging surface, the plurality of zones extending in series along the channel;
   an upper jaw pivotally coupled to the lower jaw, the upper jaw having a tissue-engaging surface opposed to the tissue-engaging surface of the lower jaw such that the two tissue-engaging surfaces are configured to grasp tissue therebetween, and a channel formed in the tissue-engaging surface of the upper jaw;
   a cutting blade having an upper portion disposed in the channel of the upper jaw, a lower portion disposed in the channel of the lower jaw, and a cutting edge disposed vertically between the upper and lower portions, the upper and lower portions being configured to contact the respective surfaces of the jaws and translate through the channels formed in the respective surfaces in response to power supplied by the motor;
   at least one metal stand-off at each zone on the lower jaw and extending vertically towards the upper jaw, the metal stand-offs being configured to prevent the electrode of the lower jaw from contacting the tissue-engaging surface of the upper jaw, and further being configured to sense impedance of tissue in contact with the respective stand-off, each electrode being configured to be switched from an on configuration to an off configuration such that energy is not delivered to the electrode when in the off configuration, and the corresponding metal stand-off being configured to measure impedance only when each electrode is in the off configuration; and
   a controller configured to be capable of adjusting a speed of the cutting blade based on the sensed impedance in real time as the cutting blade passes through each subsequent zone along the channel of the lower jaw.

10. The device of claim 9, wherein each metal stand-off is electrically isolated with respect to the other metal stand-offs.

11. The device of claim 9, wherein each metal stand-off is configured to send a pulse to the upper jaw to measure tissue impedance at the zone in which the metal stand-off is located.

12. The device of claim 9, wherein the electrode is configured to be selectively switched from being part of a current path extending between the lower and upper jaws when the jaws are in a closed position, to being isolated from current power supplied by the motor.

13. The device of claim 9, wherein the tissue-engaging surface of the upper jaw includes an electrode that is opposed to the electrode of the lower jaw.

14. The device of claim 9, wherein the plurality of zones is at least three, and there are at least three metal stand-offs, at least one in each zone.

15. The device of claim 9, wherein each metal stand-off extends from the lower jaw and through each zone of the electrode without contacting the electrode, and each metal stand-off is electrically isolated with respect to the other metal stand-offs.

16. A surgical method, comprising:
closing opposed first and second jaws of a surgical device on tissue disposed between the first and second jaws, at least the first jaw having an electrode disposed on a tissue-engaging surface of the first jaw, the electrode being segmented into a plurality of zones in series from a proximal end to a distal end of the first jaw, a protrusion at each zone and extending toward the second jaw to prevent the electrode from contacting the second jaw when not obstructed by tissue, and a cutting blade being disposed between the jaws and configured to translate through at least a portion of the jaws to transect tissue disposed between the jaws;
applying energy to the tissue disposed between the jaws;
measuring a tissue impedance at each zone of the plurality of zones sequentially through each protrusion in each of the plurality of zones, the electrode being turned off prior to measuring the tissue impedance at each zone such that energy is not delivered to the electrode when the electrode is turned off, and measuring the tissue impedance occurring only when the electrode is turned off;
operating the surgical device such that a controller of the surgical device is capable of adjusting a speed of the cutting blade as it translates through each zone of the plurality of zones in the first jaw and an amount of energy applied by each of the plurality of zones to the tissue disposed between the jaws based on the tissue impedance measured at the zones; and
turning on the electrode after measuring the tissue impedance.

17. The method of claim 16, further comprising switching the electrode between a configuration in which it is part of a current path that extends from the first jaw to the second jaw, and a configuration in which the electrode is isolated from current power supplied by a driver that powers the cutting blade.

18. The method of claim 16, further comprising mapping tissue thickness at each zone based on the measured tissue impedance at each zone.

19. The method of claim 16, further comprising:
applying energy to one or more of the one or more zones based on the tissue impedance measured at the zones;
measuring a tissue impedance for one or more of the zones in which energy was applied;
comparing the measured tissue to a threshold impedance value for each zone in which tissue impedance was measured; and
repeating the applying energy step to a zone of the one or more zones until the value of the measured tissue impedance for that zone is equal to or greater than the threshold impedance value for that zone.

20. The method of claim 16, wherein closing the opposed first and second jaws includes the protrusion at each zone extending from the first jaw and through the corresponding zone without contacting the electrode, and wherein each protrusion is electrically isolated with respect to the other protrusions.

* * * * *